US009548487B2

(12) United States Patent
Rosciano et al.

(10) Patent No.: US 9,548,487 B2
(45) Date of Patent: Jan. 17, 2017

(54) ORGANIC ACTIVE MATERIALS FOR ELECTROCHEMICAL ENERGY STORAGE

(71) Applicant: TOYOTA MOTOR EUROPE NV/SA, Brussels (BE)

(72) Inventors: Fabio Rosciano, Schaarbeek (BE); Riccardo Ruffo, Bresso (IT); Luca Beverina, Milan (IT); Mauro Sassi, Vedano Olona (IT); Matteo Marco Salamone, Brugherio (IT)

(73) Assignee: TOYOTA MOTOR EUROPE NV/SA, Brussels (BE)

(*) Notice: Subject to any disclaimer, the term of this patent is extended or adjusted under 35 U.S.C. 154(b) by 0 days.

(21) Appl. No.: 14/439,386

(22) PCT Filed: Oct. 31, 2012

(86) PCT No.: PCT/EP2012/071615
  § 371 (c)(1),
  (2) Date: Apr. 29, 2015

(87) PCT Pub. No.: WO2014/067574
  PCT Pub. Date: May 8, 2014

(65) Prior Publication Data
  US 2015/0295229 A1    Oct. 15, 2015

(51) Int. Cl.
  H01M 4/137    (2010.01)
  H01M 4/60     (2006.01)
  H01M 10/0525  (2010.01)
  H01B 1/12     (2006.01)
  C08G 61/12    (2006.01)
  C07D 519/00   (2006.01)
  H01L 51/52    (2006.01)
  H01G 11/48    (2013.01)

(52) U.S. Cl.
  CPC ............ *H01M 4/137* (2013.01); *C07D 519/00* (2013.01); *C08G 61/122* (2013.01); *C08G 61/124* (2013.01); *C08G 61/126* (2013.01); *H01B 1/127* (2013.01); *H01M 4/602* (2013.01); *H01M 4/606* (2013.01); *H01M 4/608* (2013.01); *H01M 10/0525* (2013.01); C08G 2261/11 (2013.01); C08G 2261/149 (2013.01); C08G 2261/1424 (2013.01); C08G 2261/3241 (2013.01); C08G 2261/3247 (2013.01); C08G 2261/43 (2013.01); C08G 2261/90 (2013.01); H01G 11/48 (2013.01); H01L 51/5203 (2013.01); H01M 2220/20 (2013.01); Y02E 60/122 (2013.01); Y02P 70/521 (2015.11)

(58) Field of Classification Search
  CPC .. Y02E 60/122; Y02P 70/521; H01L 51/5203; H01M 4/137
  See application file for complete search history.

(56) References Cited

U.S. PATENT DOCUMENTS 6,472,100 B1 * 10/2002 Maruta ................ H01M 4/131
                                                   429/218.1
7,045,248 B2    5/2006 Bannai et al.
2003/0096165 A1 5/2003 Nakahara et al.
2005/0042450 A1 2/2005 Sano et al.
2008/0038636 A1 2/2008 Suguro et al.
2010/0009256 A1 1/2010 Kusachi et al.
2010/0126880 A1 * 5/2010 Yu ........................ C07F 15/0026
                                                   205/775

FOREIGN PATENT DOCUMENTS

| CN | 101504971 A   | 8/2009 |
| CN | 102492118 A   | 6/2012 |
| JP | 2005-050669 A | 2/2005 |
| JP | 2010-509322 A | 3/2010 |
| JP | 2013-056959 A | 3/2013 |
| WO | 2008/057054 A1| 5/2008 |
| WO | 2013/038243 A2| 3/2013 |

OTHER PUBLICATIONS

USPTO structure search, Dec. 2015.*
Sonnenschein et al Novel Redox-Active Cyclophanes Based on 3,3'-Biindolizines: Synthesis and Chirality, J. Org. Chem. 1996, 61, 710-714, Feb. 1996.*
Czardybon, A. et al., "Synthesis, Electrochemical and Spectroelectrochemical Properties of Viologen Derivative of PEDOT," Polish Journal of Chemistry, vol. 78, 2004, pp. 1533-1541.
Liou, Guey-Shen et al., "Highly Stable Anodic Electrochromic Aromatic Polyamides Containing N, N, N', N'-Tetraphenyl-p-Phenylenediamine Moieties: Synthesis, Electrochemical, and Electrochromic Properties," Marcromolecules, vol. 41, No. 5, 2008, pp. 1667-1674.
Chen, Haiyan et al., "From Biomass to a Renewable LixC6O6 Organic Electrode for Sustainable Li-Ion Batteries," CHEMSUSCHEM, vol. 1, pp. 348-355, Jan. 2008.
Kiya, Yasuyuki et al., "4-Amino-4H-1,2,4-triazole-3, 5-dithiol a Modifiable Organosulfer Compound as a High-Energy Cathode for Lithium-Ion Rechargeable Batteries," Journal of the Electrochemical Society, vol. 154, No. 9, (2007), pp. A844-A848.
Jul. 12, 2013 Search Report issued in International Patent Application No. PCT/EP2012/071615.
Tansil et al., "Electropolymerization of intercalator-grafted conducting polymer for direct and amplified DNA detection," Chemical Communications, vol. 47, pp. 1533-1535, 2011.
Sassi et al., "Gray to Colorless Switching, Crosslinked Electrochromic Polymers with Outstanding Stability and Transmissivity From Naphthalenediimmide-Functionalized EDOT," Advanced Materials, vol. 24, pp. 2004-2008, 2012.
Bu et al., "Efficient post-polymerization functionalization of conducting poly(3,4-ethylenedioxythiophene) (PEDOT) via click'-reaction," Tetrahedron, vol. 67, pp. 114-1125, 2011.

* cited by examiner

Primary Examiner — Gregory Listvoyb
(74) Attorney, Agent, or Firm — Oliff PLC

(57) ABSTRACT

A compound having the structure Red-R-M, wherein: Red is a redox center; R is a bridging group; and M is a monomer giving rise to an electronically conductive polymer, is provided. Also provides are polymers obtained by polymerization of such compounds and uses in electronic devices of such polymers, for example uses in batteries.

9 Claims, 10 Drawing Sheets

Viologens

Rylen bis-imides n = 0,1

Violenes

III

Where het-1 and Het-2 Corresponds to

Anthraquinones m = 0, 4, 5, 6 m = 0, 4, 5, 6

X = O, S

R' = represents the Bridge-Polymer functionalization

ORGANIC ACTIVE MATERIALS FOR ELECTROCHEMICAL ENERGY STORAGE

The present invention relates to compounds containing both a redox centre and a monomer able to be polymerized to produce an electrically conductive polymer, the redox centre and monomer being separated by a bridging group, as well as to polymers obtained by polymerization of such compounds and uses in electronic devices of such polymers, for example uses in batteries.

BACKGROUND TO THE INVENTION

Rechargeable (secondary) batteries are of increasing importance both in the consumer electronics field (as components of e.g. mobile telephones and laptop computers) as well as in vehicle and aerospace applications. An example of a rechargeable battery is the lithium-ion battery in which lithium ions in the electrolyte move from the negative electrode to the positive electrode during discharge (and move in the reverse direction during charging). FIG. 2 shows an example of an electrochemical device used to store energy (a battery) containing a positive electrode material and a negative electrode material separated by separator containing a liquid, gel, polymeric or solid electrolyte, with a current collector used on both sides of the battery to carry the electrical energy.

Organic materials can be used effectively to store charge. Thus, US 2010/0009256 and US 2008/0038636 relate to the use of a polyradical material, a polymer with pendant nitroxyl radical groups, as an electrode active material. US 2003/0096165 discloses materials containing polyradicals of various structures for use in secondary batteries, and U.S. Pat. No. 7,045,248 focuses on boron or sulfur radicals. Such "Organic Radical Batteries" (ORBs) show good performance in that they offer high power density. However, the materials are not electronically conductive, hence to obtain such performance it is needed to add up to 50% of carbon in the electrode formulation. This causes a sharp decrease of both volumetric and gravimetric energy density.

Another example of organic material used for energy storage was presented by researchers in Amiens (Chem Sus Chem DOI: 10.1002/cssc.200700161). These materials provide excellent charge storage (very high capacity) but fall short of the rate capability needed to provide high power density.

Organosulfur compounds (3 Electrochem Soc 2007 154 A844-A848) have been proposed as other organic active materials for energy storage, but their performance is seriously hampered by their solubility in the electrolyte.

Problems to be Solved

In view of the state of the art, there was a need to develop new organic materials that can be used to store electrochemical energy in a device, e.g. a battery. It is desired for the material to have as many as possible of the following properties:
1) Be a good electronic conductor,
2) Provide high energy density,
3) Provide high power density,
4) Be insoluble in the standard Li-ion electrolytes.

SUMMARY OF THE INVENTION

The present invention consists in a new class of materials which can store charge, but are also excellent electronic conductors, thus not needing large amounts of conductivity enhancers in the electrode formulation.

Embodiments of the present invention provide materials that can supply high power density and provide almost constant charge at very high charge and discharge rates. Embodiments of the present invention also provide materials that are not soluble in standard Li-ion battery electrolytes, thus giving a long lifetime to a Li-ion battery-based device containing the materials.

The present invention relates to a compound containing the structure Red-R-M, wherein:
  Red is a redox center;
  R is a bridging group; and
  M is a monomer giving rise to an electronically conductive polymer.

In preferred embodiments of the present invention, the redox center contains a group selected from the group consisting of: arylenebisimides, indolizines, viologens, violenes, anthraquinones. The compound of the invention may advantageously show one of the following structures where, respectively, the redox centre is an arylenebismide or a (bis)indolizine:

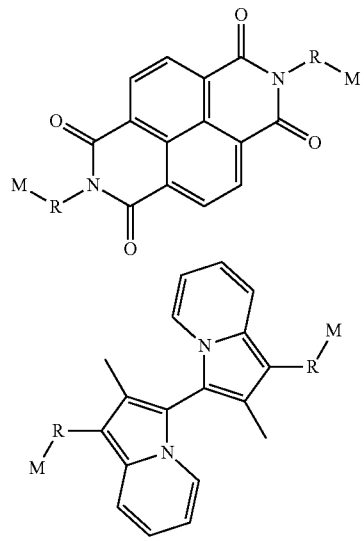

In preferred embodiments of compounds of the present invention, the monomer M contains a group selected from the group consisting of: thiophene, pyrrole, paraphenylenvinylene, furan, carbazole, silole, fluorene. In a particularly preferred embodiment which is experimentally exemplified herein, the compound contains a 3,4-ethylenedioxythiophene (EDOT) group, with a thiophene unit that may be converted into an electrically conductive polymer backbone.

In preferred embodiments of compounds of the present invention, the bridge R contains a linear alkylene chain or branched alkylene chain or glycolic chain, or a combination of functional groups selected among the following: —C(=O)—, —C(=S)—, —O—C(=O)—, —O—C(=S)—, —O—C(=O)—O—, —(C=O)—O—, —C(=S)—O—, —C(=S)—S—, —C(=O)—NR'— or —C(=S)—NR'— where R' is H or alkyl, —SO, —SO$_2$, or a combination of any linear alkylic chain or branched alkylic chain or glycolic chain separated by one or more of the said functional groups.

Two exemplary compounds of the invention, whose worked syntheses are presented hereinafter, have the structures shown below:

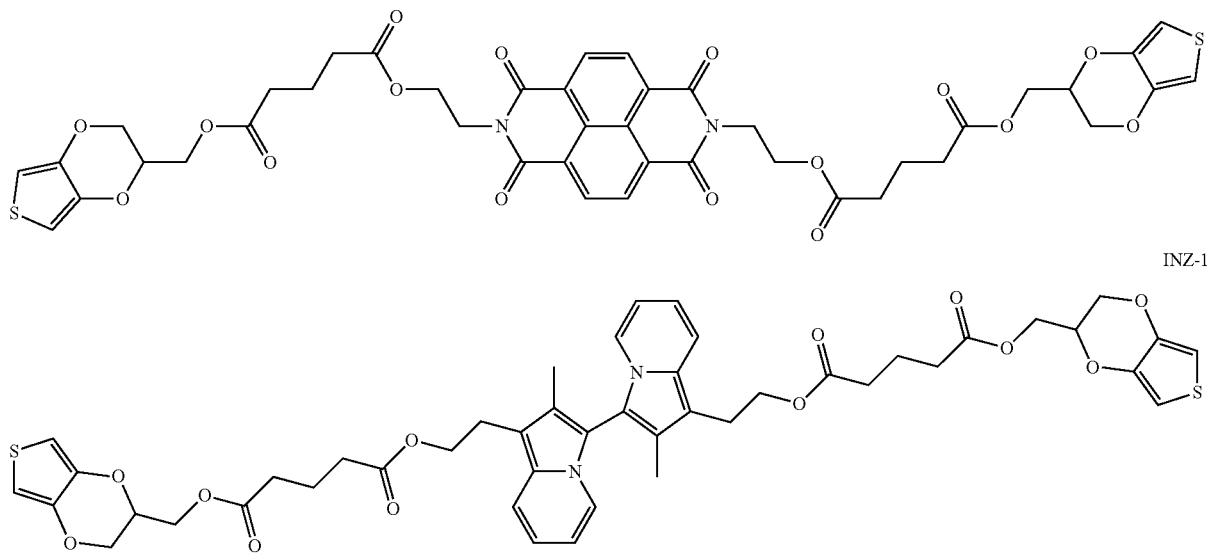

DETAILED DESCRIPTION OF THE INVENTION

An important feature of the present invention is in the coupling of a molecule able to store charge to an electrically conductive polymeric backbone.

In another aspect, the present invention relates to a polymer obtained by polymerization of a compound containing the structure Red-R-M as detailed above. In a further aspect, the present invention relates to the use of such a polymer to store electrochemical energy. In a further aspect, the present invention relates to the use of such a polymer in a lithium-ion battery.

Figure 3:
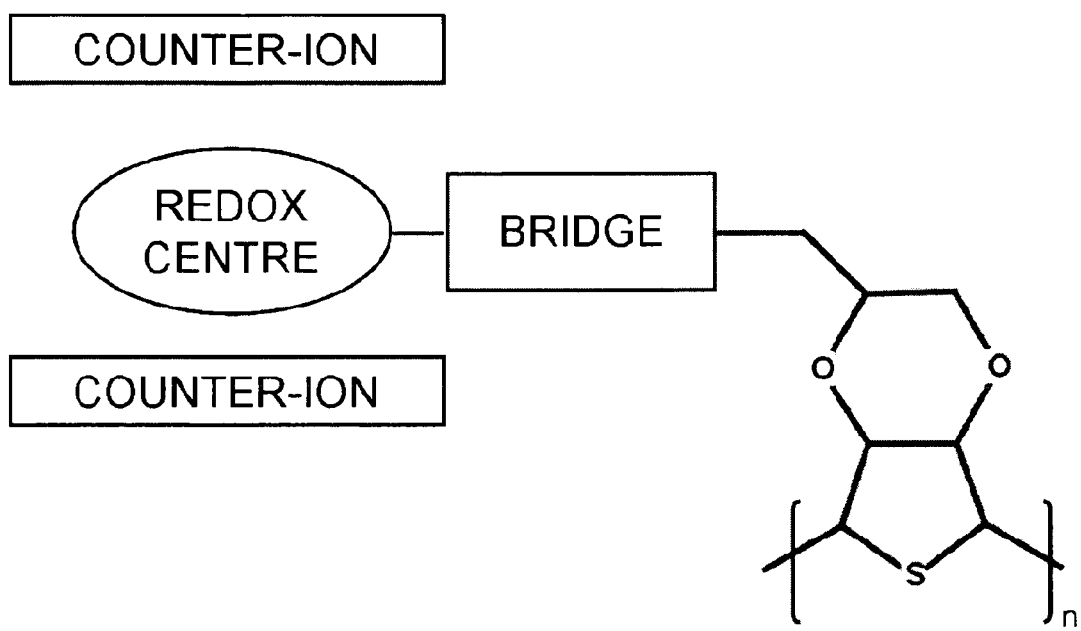
FIG. 3 is a schematic view of polymer materials according to the present invention, illustrated for a polymeric backbone based on PEDOT.
Figure 4:
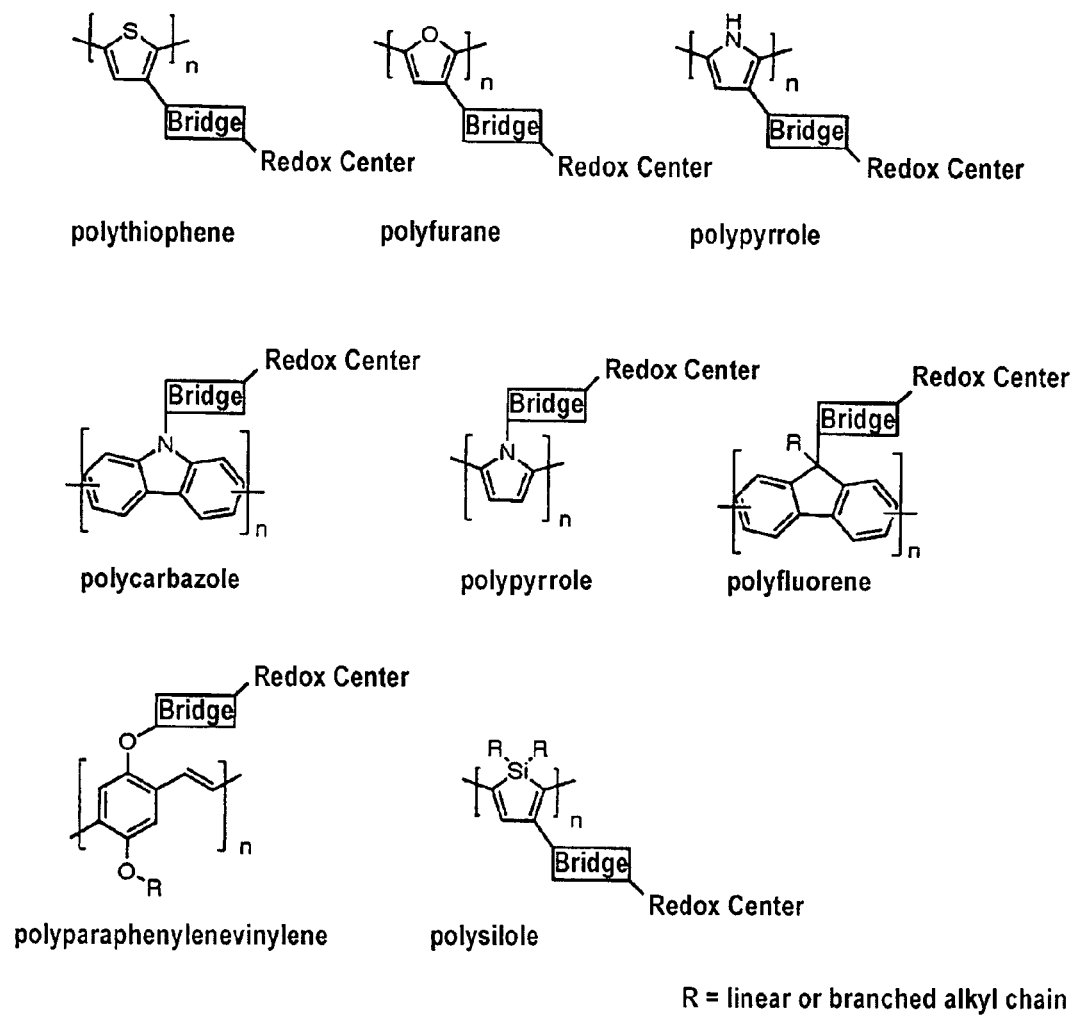
FIG. 4 is a schematic view of polymer materials according to the present invention, illustrated for a polymeric backbone based on various monomer types envisaged in the invention.
Figure 5:
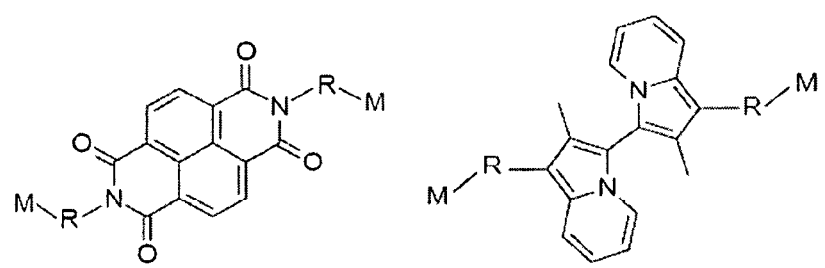
FIG. 5 illustrates some specific redox centres that may be used in exemplary compounds and polymer materials of the present invention.

The structure of the polymer materials of the present invention can be generalized as containing three elements: a polymeric electronically conductive backbone, electrochemically active redox centres and organic bridges linking the other two elements i.e the redox centres to the polymeric electronically conductive backbone. An illustrative and non-limiting example is given in FIG. 3. In this example the polymeric backbone is PEDOT (poly(3,4-ethylenedioxythiophene)) i.e. a polymer derived from a 3,4-ethylenedioxythiophene (EDOT) group. This is a preferred material for the polymeric electronically conductive backbone in the present invention, but other electronically conductive polymers can also be used. As an example, possible polymers could be but are not limited to: polythiophenes, polypyrroles, polyparaphenylenevinylenes, polyfurans, polycarbazoles, polysiloles, polyfluorenes, and copolymers obtained by combining repeating units of the above mentioned homopolymers. Representative structures, as well as an indication of the functionalization site bearing the redox center, are shown in FIG. 4. For example, where the monomer unit contains a nitrogen atom, the latter may be functionalized with, for example, alkyl groups or other types of groups constituting bridging groups in the compounds and polymers of the present invention. In other systems, such as the five-membered ring monomers thiophene, furan, pyrrole and silole, the 3-position of the ring may be used to link through a bridge to a redox centre. For example, monomers containing such a core five-membered ring exist for which the 3-position of the ring is linked to a functional group such as an —OH or —CO$_2$H group, which may then be linked to the other parts of the compounds of the invention.

Polymerization of the monomer units may be carried out according to techniques known in the art for such monomers giving rise to electrically conductive polymer backbones. As an example, when polymerizing thiophene monomers, in a typical polymerization process, a suitable oxidizing agent is added, which may in particular give rise to polymers in which hydrogen atoms are removed from thiophene rings as the latter are joined together to produce polymer chains. As a suitable but merely illustrative and non-limiting example of an oxidizing agent that may be used to induce polymerization of thiophene-containing monomers to give electrically conductive polymers, one may cite Baytron-CB-40, which is iron (III) tosylate.

The same type of polymerization protocol may be applied for the polymerization of thiophene, pyrrole, furane and carbazole derivatives shown in FIG. 4. Fluorene, polyparaphenylenevinylene and silole derivatives may be polymerized starting from suitable halogenated and/or organotin and/or organoboron derivatives using either nickel, copper or palladium catalyzed coupling reactions.

Various structures are possible for the bridge "R" in compounds of the present invention. As an example, the bridge can be made using any linear alkylene chain or branched alkylene chain or glycolic chain (alkylene or branched alkylene chain with one or more —$CH_2$— or —CHR'— or —CRR"— groups being replaced by an oxygen atom, where R' and R" are alkyl groups) or a combination of them, the alkylene and/or glycolic chain(s) being optionally separated by functional groups selected among the following: —C=O, —C=S, —O(C=O), —O(C=S), —O(C=O)O, —(C=O)O, —(C=S)O, —(C=S)S, —(C=O)NR' or —(C=S)NR' wherein R' is H or alkyl such as C1-C6 alkyl, —SO, —$SO_2$. It is also possible for the bridge to be wholly constituted by such functional groups. In an advantageous embodiment, the minimum number of atoms counted directly along the atomic chain between the redox centre, in particular between the ring atom of a redox centre to which bridging group "R" is joined on the one hand, and the monomer M, in particular the ring atom of monomer M to which bridging group "R" is joined on the other hand, is between 1 and 15 atoms, preferably between 3 and 11 atoms, and more preferably between 5 and 9 atoms.

It is also envisaged in embodiments of the present invention that the bridging group may include a divalent aryl, substituted aryl, heteroaryl or substituted heteroaryl group. The substituents on the divalent (hetero)aryl ring may include electron-rich groups, or electron-withdrawing groups such as halogen groups, including fluorine atoms. In the event that the (hetero)aryl ring is bound directly to the redox centre, this may be considered to be part of the redox centre itself.

Figure 6:
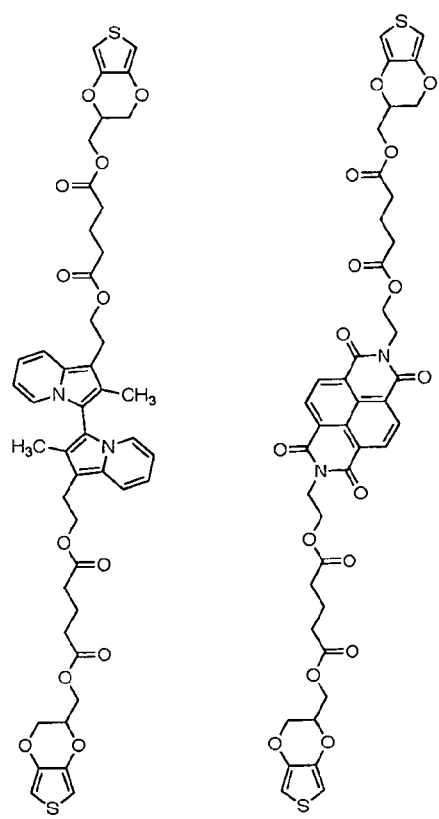
FIG. 6 illustrates some specific compounds of the present invention.

Two specific illustrative and non-limiting examples of compounds according to the present invention which have ester-type bridge are shown in FIG. 6. These illustrative exemplified compounds show the structure (Redox centre)-[Bridge-EDOT]$_2$. These symmetrical structures, with two monomers M positioned around a central redox centre, appear to provide higher electrochemical stability compared to ones in which there is a single pendant monomer M. Structures of the type (Redox centre)-[Bridge-EDOT]$_2$ therefore constitute a preferred embodiment according to the present invention. However, providing that there is at least one pendant M group, a functioning polymer material of the present invention may be obtained, and thus there may be only one, or three, or more, bridges and conductive monomer groups around the redox centre.

Figure 7:
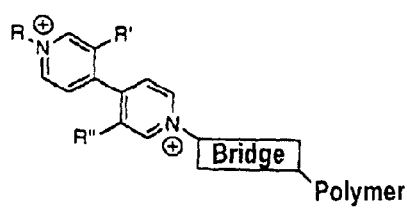
FIG. 7 illustrates various redox centres that may be used in compounds and polymer materials of the present invention
Figure 7:
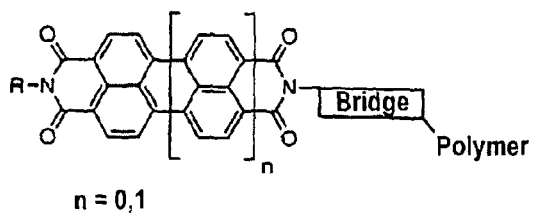
Figure 7:
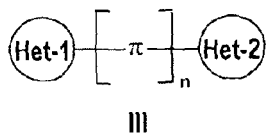
Figure 7:
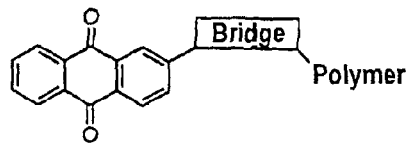
Figure 7:
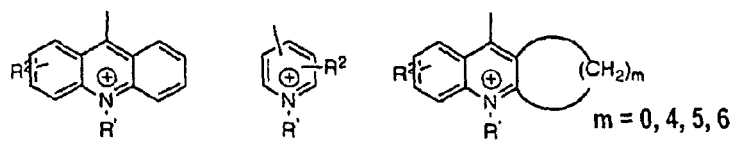
Figure 7:
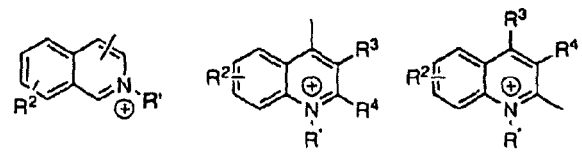
Figure 7:
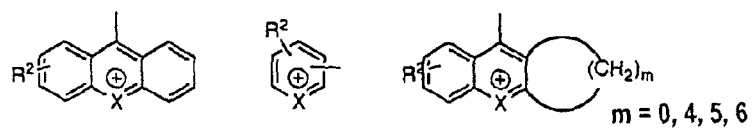
Figure 7:
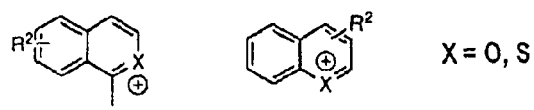
Figure 8:
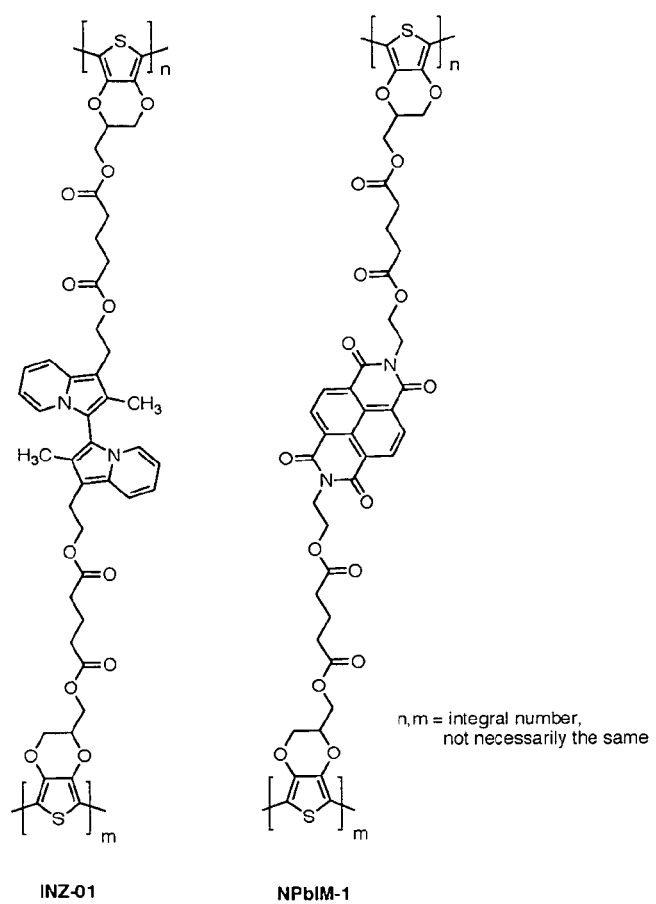
FIG. 8 illustrates some specific polymers of the present invention.

As redox centers, molecules which can be oxidized or reduced reversibly within the potential window of interest for organic batteries may be used. Amongst oxidizable centers are electron rich heterocyclic amines. Among reducible centers are: viologens, violenes, anthraquinones, arylenebisimides, and related compounds. FIG. 7 shows representative examples of the above mentioned structures. In a number of advantageous embodiments, the redox centre contains one or two (most commonly two) nitrogen atoms which may be functionalized with, for example, alkyl groups or other types of groups constituting bridging groups in the compounds and polymers of the present invention.

As mentioned above, in some possible exemplary embodiments of the present invention, a substituted or unsubstituted aryl or heteroaryl ring may be bound directly to the redox centre, for example, bound in particular to a nitrogen atom of the redox centre. The divalent substituted or unsubstituted aryl or heteroaryl ring may then have an effect on the properties of the redox centre, for example the substituents on the divalent (hetero)aryl ring may include electron-rich groups, or electron-withdrawing groups such as halogen groups, including fluorine atoms. In such a case where a (hetero)aryl ring is bound directly to the redox centre, the ring may be conceptually considered to be part of the redox centre itself, rather than considering that the (hetero)aryl ring atoms are part of the bridging group.

Changing redox centers and bridges in compounds in the invention has notably the following two effects: (1) defining the electrochemical potential at which the molecule is active and (2) defining the molecular weight of the material, thus influencing the volumetric and gravimetric energy and power densities. For example adopting Electron-Withdrawing Groups (EWG) will increase the potential, allowing the preparation of materials suitable to be used as positive electrode materials (cathodes).

The polymeric backbone of polymers of the present invention has the primary function to serve as a fast electronic conductor, but it can also store charge either by charge transfer or by adsorption (capacitive behavior). In the present invention, a preferred electrically conductive polymer backbone is PEDOT.

Figure 1:
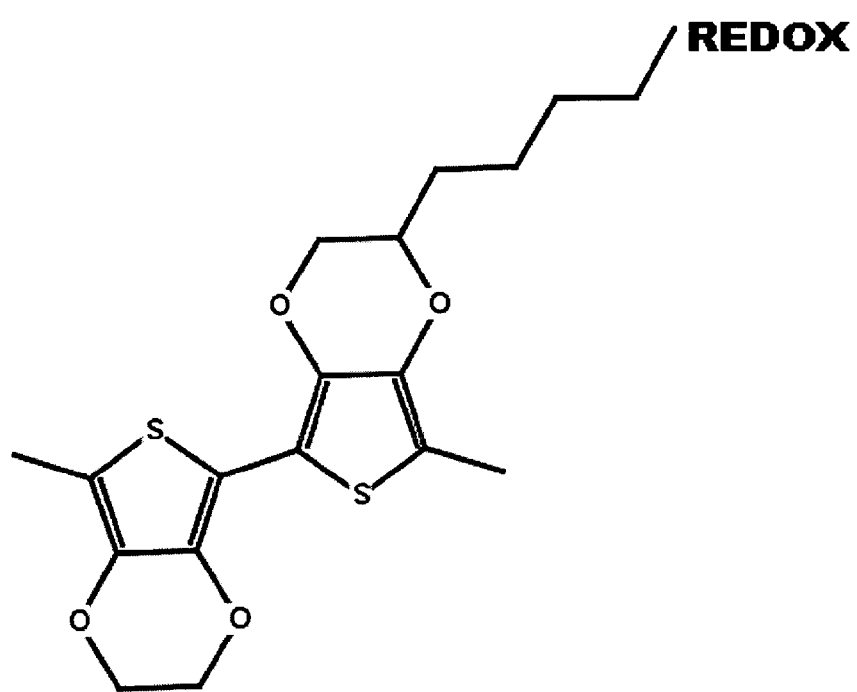
FIG. 1 is a schematic diagram showing an illustrative example of electroactive polymers with a PEDOT polymeric backbone attached to a redox centre via an alkylene bridge.
Figure 2:
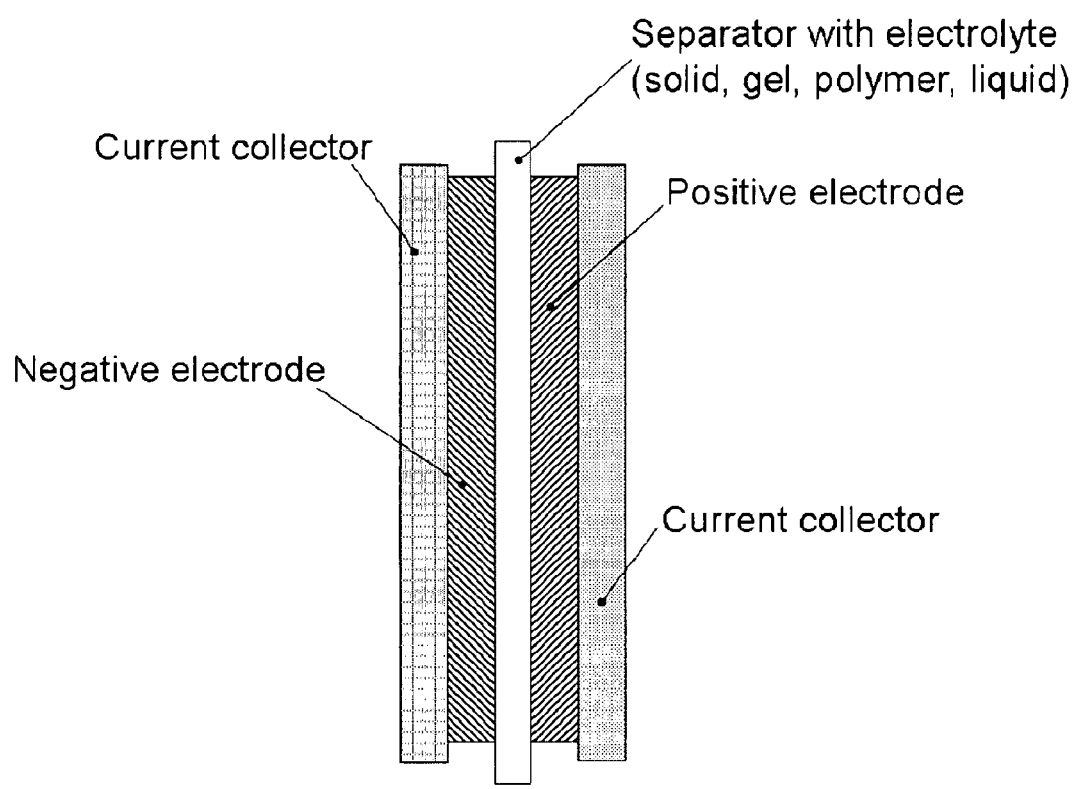
FIG. 2 is a schematic drawing of a battery.

The polymer materials of the present invention may be used in an electrochemical device to store energy (e.g. a battery). The materials may be used as part of a composite electrode. The materials may be used either as a positive electrode material, negative electrode material, or both, separated by a liquid, gel, polymeric or solid electrolyte. An electrolyte allows the passage of ions from one end of the device to the other, and ions may be stored using materials of the invention. At the same time, electrons flow from one end of the battery to the other, the direction of the flow depending if the device is being used to power an external load or if it is being recharged. A current collector will appropriately be used on both sides of the battery to carry the electrical energy. FIG. 2 has an example of a device into which materials of the present invention may be incorporated. The present invention could be used in batteries where the electrolyte contains mono- and divalent cations and anions, both organic and inorganic. The choice of electrolyte can include, but is not limited to, lithium ions, sodium ions, potassium ions, tetrabutylammonium ions, hexafluorophosphate ions, perchlorate ions, tetrafluoroborate ions, bistrifluoromethanesulfoneimide ions (TFSI). The solvent for the electrolyte will be chosen according to the operation potential of the electrode materials and can contain, but is not limited to, ethylene carbonate, dimethylcarbonate, propylenecarbonate, acetonitrile.

Examples

Monomer Preparation Procedures

A1. Synthesis of INZ-0

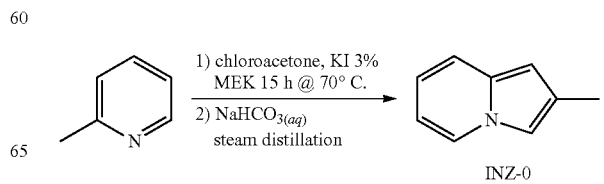

In an amber glass 50 ml RBF, equipped with CaCl$_2$ guard tube, chloroacetone (10.34 ml, 11.91 g, 128.7 mmol) was added to a solution of 2-picoline (10.00 g, 107.3 mmol) in 2-butanone (25 ml) followed by KI (641 mg, 3.86 mmol). The mixture was heated to 70° C. for 15 h, cooled to RT and kept under stirring for 12 h. Et$_2$O (25 ml) was added to the mixture and the obtained suspension was filtered on an Hirsh funnel. The deliquescent dark solid was transferred to a 250 ml RBF and dissolved in 125 ml of water. The solution was kept under stirring and NaHCO$_3$ was slowly added observing gas evolution. The mixture was steam distilled obtaining a suspension of the pure product in the distillate. The distillate was filtered on an Hirsh funnel and the white solid was dried under reduced pressure at room temperature (8.305 g, 63.3 mmol, yield 59%).

A2. Synthesis of INZ-1

Synthesis of 9

Chloroacetone (8.09 g, 87.40 mmol) was dropwise added to a solution of 2-propanolpyridine (10.00 g, 72.89 mmol) in 2-butanone (25 ml). KI (435 mg, 2.62 mmol) was added and the mixture was heated to reflux for 24 h. The mixture was cooled to RT and Et$_2$O (100 ml) was added. The solvent was decanted and the residue was transferred to a 500 ml RBF. The organic phase was further extracted with 4×50 ml of water collecting the aqueous phase. Under N$_2$ atmosphere, NaHCO$_3$ was slowly added under stirring to the aqueous mixture observing a vigorous gas evolution. The mixture was heated to reflux for 90 min and cooled to RT. The dark mixture was extracted with 5×100 ml of Et$_2$O. The organic

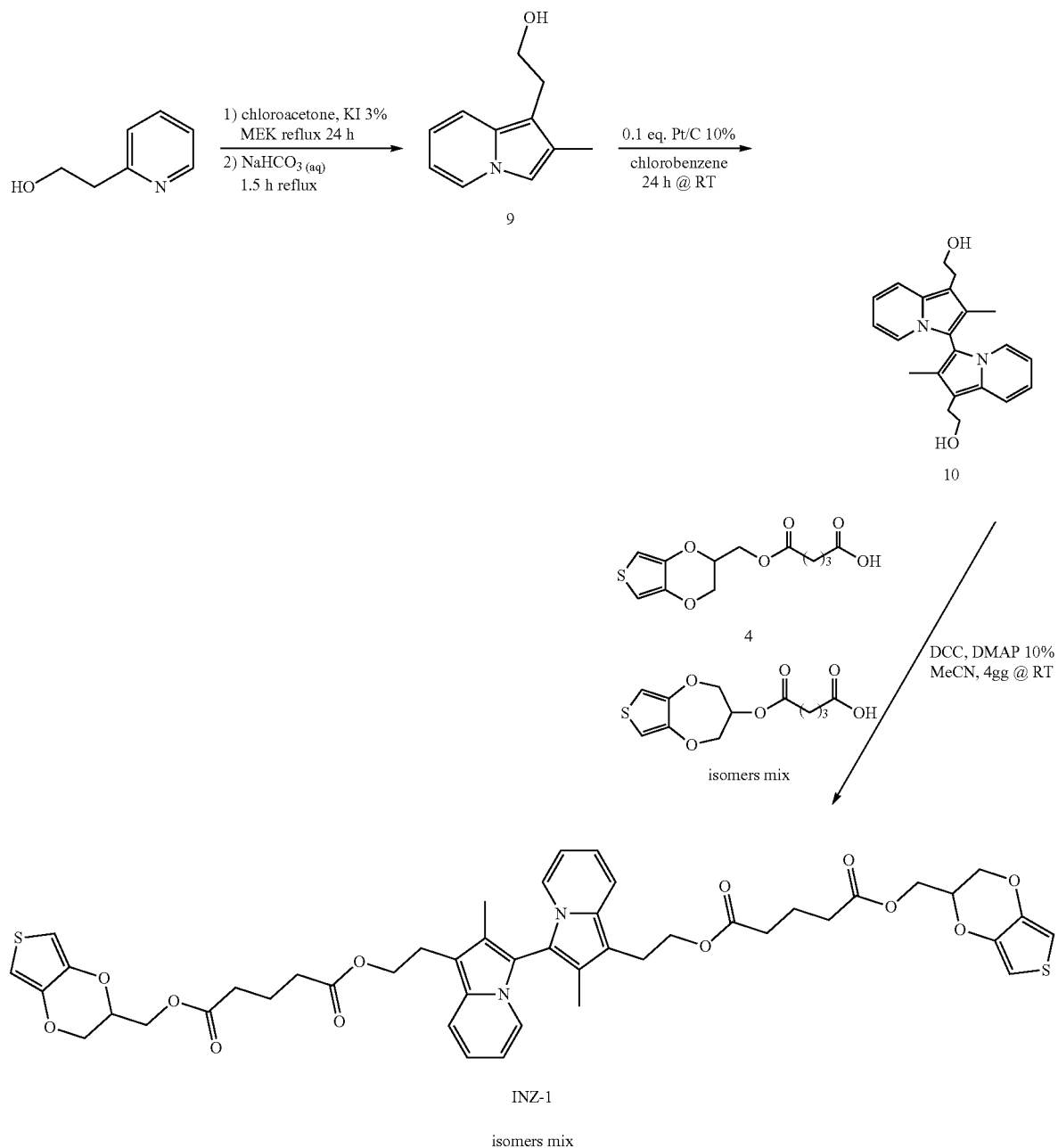

phase was collected, washed with brine (50 ml), dried over Na$_2$SO$_4$ overnight and evaporated under reduced pressure. The residue was purified by filtration on a silica plug (eluent: CH$_2$Cl$_2$/AcOEt 1:1). Product was obtained as a pale yellow oil after solvent evaporation under reduced pressure (4.200 g, 23.97 mmol, yield 33%).

$^1$H NMR (500 MHz, Acetone-d$_6$) δ [ppm]: 7.98 (d, J=7.0 Hz, 1H), 7.31 (d, J=9.0 Hz, 1H), 7.23 (s, 1H), 6.55 (t, J=8.3 Hz, 1H), 6.36 (t, J=6.7 Hz, 1H), 3.68-3.64 (m, 2H), 3.54 (t, J=5.7 Hz, 1H), 2.93 (t, J=7.4 Hz, 2H), 2.25 (s, 3H); $^{13}$C NMR (125.7 MHz, Acetone-d$_6$) δ [ppm]: 131.52, 125.66, 124.18, 117.47, 116.12, 111.68, 109.77, 109.10, 63.46, 28.73, 10.72.

Synthesis of 10

A mixture of 9 (4.100 g, 23.39 mmol) and Pt/C 10% (4.56 g, 2.34 mmol) in chlorobenzene (220 ml) was stirred at RT in an open 500 ml round bottom flask for 24 h. The mixture was filtered to remove the catalyst washing with chlorobenzene and the filtrate was evaporated under reduced pressure. The residue was purified by chromatography on silica gel (eluent: CH$_2$Cl$_2$/AcOEt 2:3), obtaining a clear oil after solvent evaporation under reduced pressure. The residue was triturated with Et$_2$O (10 ml) obtaining pure product as pale greenish solid (901 mg, 2.58 mmol, yield 22%, m.p.: 148-150° C.).

$^1$H NMR (500 MHz, Acetone-d$_6$) δ [ppm]: 7.51 (d, J=9.0 Hz, 2H), 7.22 (d, J=7.0 Hz, 2H), 6.71 (t, J=7.5 Hz, 2H), 6.44 (t, J=7.1 Hz, 2H), 3.80-3.76 (m, 4H), 3.61 (t, J=5.8 Hz, 2H), 3.06 (t, J=7.1 Hz, 4H), 2.11 (s, 6H); $^{13}$C NMR (125.7 MHz, Acetone-d$_6$) δ [ppm]: 132.50, 126.13, 123.62, 117.82, 117.07, 112.46, 110.47, 109.60, 63.42, 29.03, 10.46.

Synthesis of INZ-1

Under N$_2$ atmosphere, MeCN (13 ml) was added to a mixture of 10 (350 mg, 1.004 mmol), 4 (672 mg, 2.35 mmol), DCC (515 mg, 2.49 mmol) and DMAP (27 mg, 0.22 mmol). EDOT derivatives 4 can be obtained by the methods disclosed in Italian patent application TO2011A000830 filed 15 Sep. 2011, sharing common inventors with the present application. The mixture was kept under stirring at RT for 4 days and filtered washing with MeCN. The filtrate was collected, evaporated under reduced pressure and purified by cromatography on silica gel (eluent: CH$_2$Cl$_2$/AcOEt 9:1). Product was obtained as a greenish oil after solvent evaporation under reduced pressure at 50° C. (499 mg, 0.564 mmol, yield 56%).

$^1$H NMR (500 MHz, Acetone-d$_6$) δ [ppm]: 7.54 (d, J=9.0 Hz, 2H), 7.26-7.24 (m, 2H), 6.78-6.75 (m, 2H), 6.48-6.44 (m, 6H), 4.37-4.27 (m, 12H), 4.09-4.04 (m, 2H), 3.18 (t, J=7.1 Hz, 4H), 2.40-2.34 (m, 8H), 2.13 (d, J=1.2 Hz, 6H), 1.86 (qui, J=7.3 Hz, 4H).

A3. Synthesis of NPBIM-1

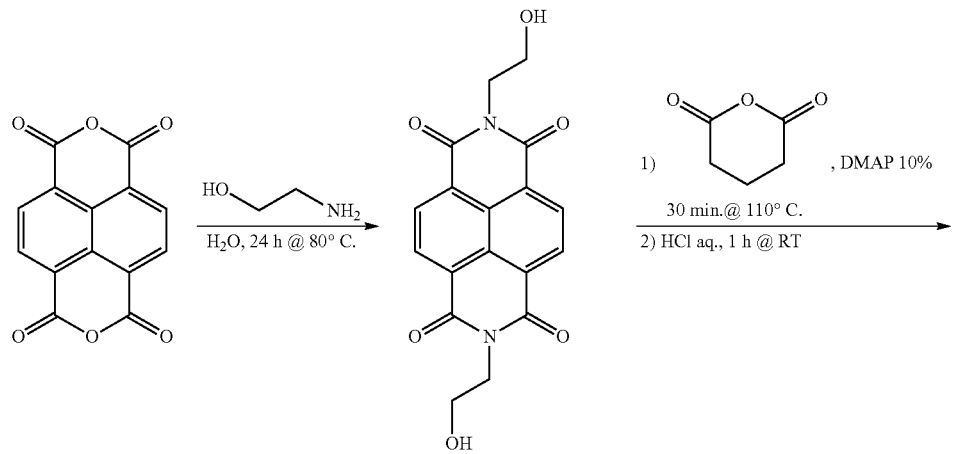

11

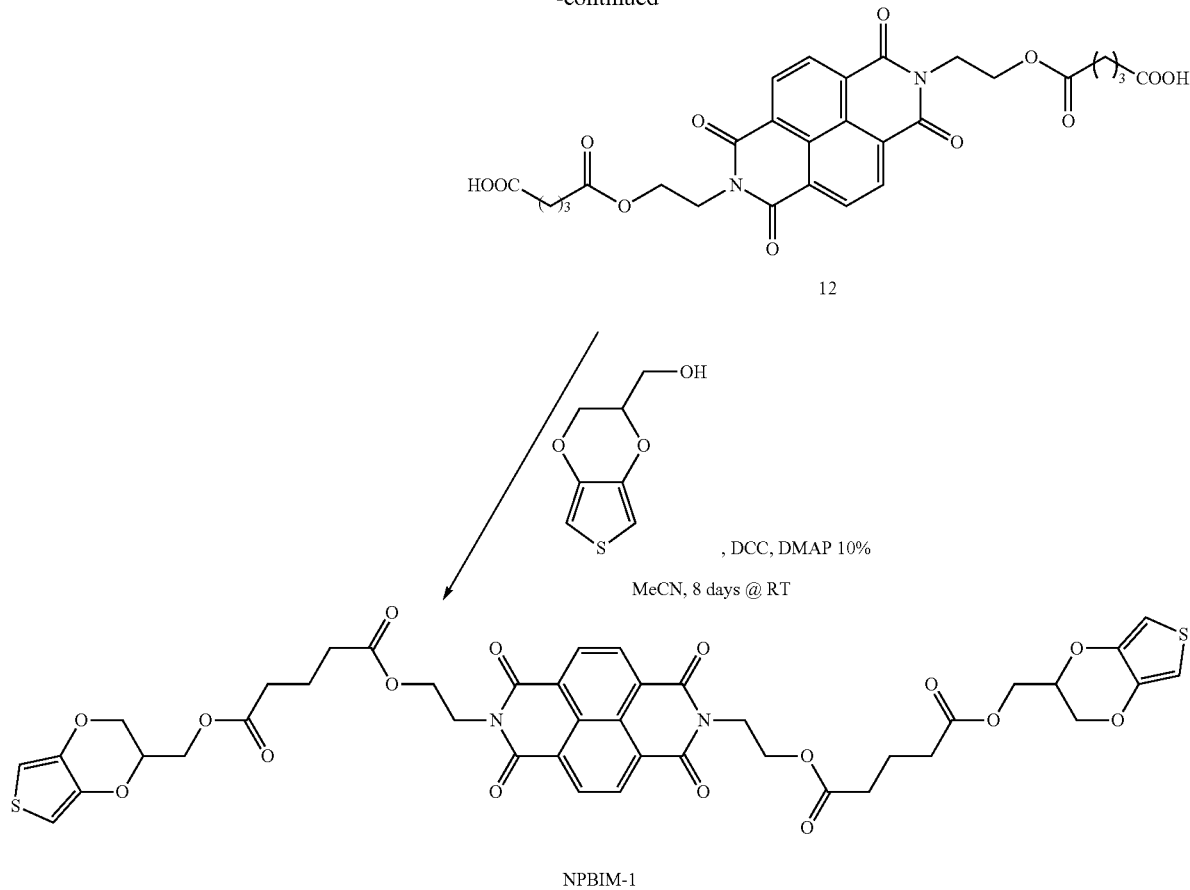

Synthesis of 11

Ethanolamine (4.759 g, 77.92 mmol) was dropwise added to a suspension of 1,4,5,8-Naphthalenetetracarboxylic dianhydride (5.226 g, 19.48 mmol) in water (60 ml) and the mixture was heated to 80° C. for 24 h. Mixture was cooled to RT and product was collected by filtration on a Buechner funnel washing with water followed by acetone. Residual solvent was evaporated under reduced pressure at 50° C. obtaining product as a pale brown solid (5.785 g, 17.73 mmol, yield 91%., m.p.: 325° C. (lit. 321-323° C.)).

Synthesis of 12

In a test tube, a mixture of 11 (3.000 g, 9.20 mmol), glutaric anhydride (21.6 g, 184 mmol) and DMAP (112 mg, 0.920 mmol) was heated to 110° C. for 30 min. The mixture was poured in 75 ml of water and acidified adding 1 ml of $HCl_{(aq.)}$ 37%. The obtained suspension was stirred at RT overnight and filtered on an Hirsh funnel washing with water followed by few ml of EtOH. Product was purified by crystallization from cyclohexanone and residual solvent was evaporated under reduced pressure. Pink solid (3.168 g, 5.44 mmol, yield 59%, m.p.: 220° C.).

$^1$H NMR (500 MHz, DMSO-$d_6$) δ [ppm]: 12.04 (s, 2H), 8.65 (s, 4H), 4.35 (s, 8H), 2.27 (t, J=7.3 Hz, 4H), 2.17 (t, J=7.4 Hz, 4H), 1.65 (qui, J=7.4 Hz, 4H).

Synthesis of NPBIM-1

Acetonitrile (35 ml) was added to a mixture of 12 (3.160 g, 5.42 mmol), EDOT-MeOH (2.33 g, 13.53 mmol), DCC (2.44 mg, 11.82 mmol) and DMAP (89 mg, 0.74 mmol). EDOT-MeOH is a commercial product (Hydroxymethyl EDOT) available from Sigma Aldrich (product reference #687553). The mixture was kept under stirring at RT for 8 days and filtered washing with MeCN. The filtrate was collected and evaporated under reduced pressure. The residue was purified by cromatography on silica gel (eluent: $CH_2Cl_2$/AcOEt 7:3). Solvent was evaporated under reduced pressure, and the residue was triturated with $Et_2O$ obtaining product as a pale yellow solid (1.304 g, 1.46 mmol, yield 27%, m.p.: 124-125° C.).

$^1$H NMR (500 MHz, $CDCl_3$-$d_6$) d [ppm]: 8.77 (s, 4H), 6.34-6.32 (m, 4H), 4.52-4.50 (m, 4H), 4.48-4.46 (m, 4H), 4.36-4.32 (m, 2H), 4.31-4.24 (m, 4H), 4.21-4.18 (m, 4H), 4.03-3.99 (m, 2H), 2.41 (t, J=7.3 Hz, 4H), 2.34 (t, J=7.2 Hz, 4H), 1.90 (qui, J=7.3 Hz, 4H); $^{13}$C NMR (125.7 MHz, $CDCl_3$-$d_6$)$_d$ [ppm]: 172.90, 172.62, 163.05, 141.23, 141.05, 131.29, 126.98, 126.63, 100.21, 100.11, 71.49, 65.65, 62.37, 61.72, 39.85, 33.01, 32.97, 19.81.

Polymer Preparation Procedures

B1. Polymerization of INZ-0

Under N2 atmosphere, N-methyl-imidazole (1.313 g, 16.00 mmol) and Baytron-CB-40 (21.7 g, 15.2 mmol) were added to a stirred solution of 2-methylindolizine (INZ-0, 1.000 g, 7.62 mmol) in dry MeCN (40 ml). The mixture was heated to reflux for 7.5 h, cooled to RT and kept under stirring for 3 days. The precipitate was collected by filtration as a dark solid. Product was sonicated and filtered twice with MeCN. The same procedure was repeated with MeOH (2×50 ml). The product was finally filtered and washed with fresh MeOH followed by $Et_2O$. Residual solvent was removed under reduced pressure at 40° C. Dark solid (1.160 g).

B2. Polymerization of NPBIM-1
Procedure A (Batch P-NPBIM-1B)
Under N₂ atmosphere, anhydrous benzonitrile (5 ml) was added to a mixture of NPBIM-1 (1.000 g, 1.122 mmol) and anhydrous Fe(OTs)₃ (2.979 g, 5.231 mmol) in a Schlenk flask. The flask was sealed and heated to 145° C. for 24 h. The mixture was cooled to RT and poured in a cellulose extraction thimble. The solid residue was extracted with MeCN in a Soxhlet apparatus until a colourless extract was obtained. The solid was further extracted with CHCl₃ followed by MeOH. The black solid residue in the thimble was dried under reduced pressure at 50° C. for 12 h and collected (737 mg).
Procedure B (Batch p-NPBIM-2B)
A suspension of NPBIM-1 (735 mg, 0.835 mmol) and anhydrous Fe(OTs)₃ (2.189 g, 3.845 mmol) in a mixture of dry CHCl₃ (20 ml) and anhydrous MeCN (10 ml) was reflux for 14 h under N₂ atmosphere. The light yellow mixture turns to green and then to blue. The mixture was cooled to RT and poured in a cellulose extraction thimble. The solid residue was extracted in a Soxhlet apparatus with CHCl₃ followed by MeOH till colourless extracts were obtained. The dark blue solid was collected and residual solvent was removed under reduced pressure at 65° C. (150 mg).
Testing of Compounds and Materials According to the Present Invention The data in FIG. 9 was obtained in a Li-battery configuration. Poly-NPbIm-1 was used to prepare a composite electrode (72% by weight) along with graphite (SFG6, Timcal, 26% by weight), Carboxymethylcellulose (Sigma, 1%) and Styrene-Butadiene Rubber (Targray, 1%) in water. The resulting slurry was cast on an aluminum foil with a wet thickness of 300 μm. The electrode was dried in atmosphere at 80° C. overnight. From the foil, 16 mm diameter circular electrodes were cut and used to build coin cells. The counter electrode in the coin cell was metallic lithium, the separator was glass fiber and the electrolyte was 1M LiClO₄ in Ethylene Carbonate/Dimethylcarbonate 1:1 in weight. The coin cells were tested using a BioLogic VMP3 charge-discharge machine.

Figure 10:
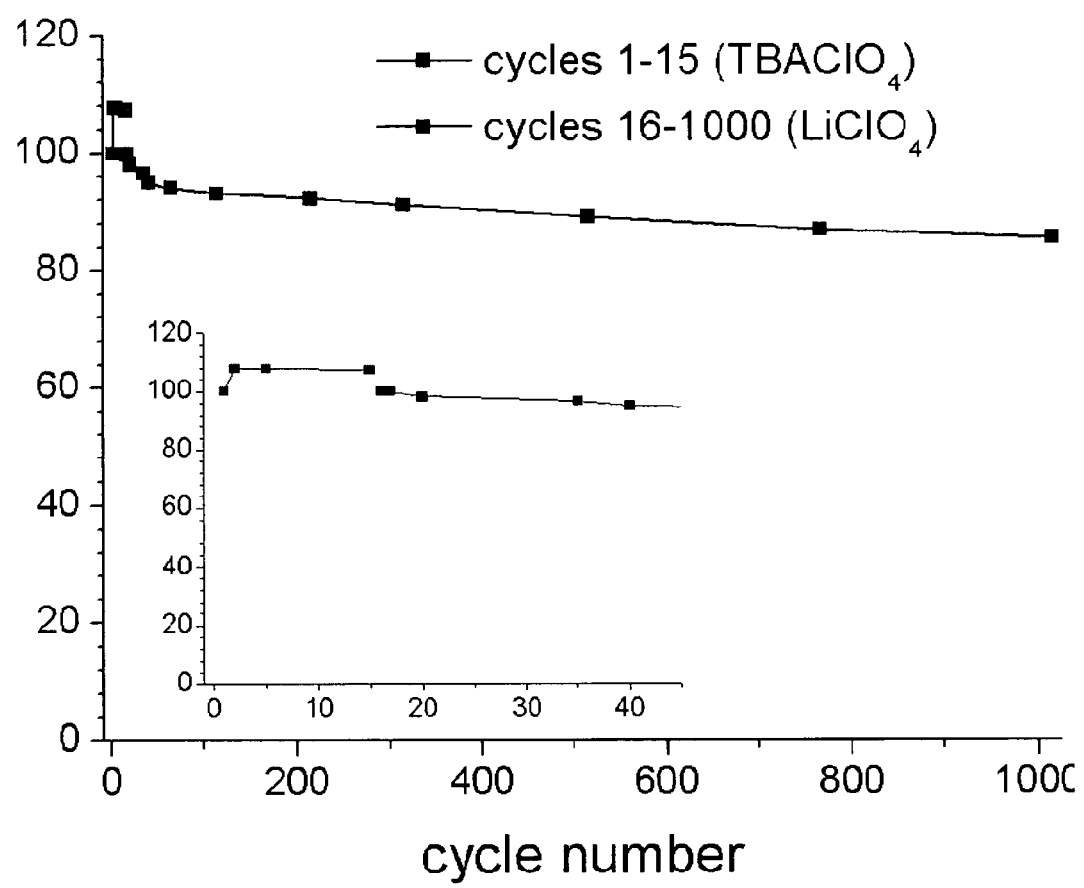
FIG. 10 illustrates long-term stability of Poly-NPbIM-1.

The data in FIG. 10 was obtained in a flooded cell where the working electrode was a film of Poly-NPbIm-1 electropolymerized on an aluminum foil. The counter electrode was Pt and the reference electrode was Ag/Ag⁺. The electrolyte was Acetonitrile/TBAClO₄, changed later to Acetonitrile/LiClO₄.

Figure 9:
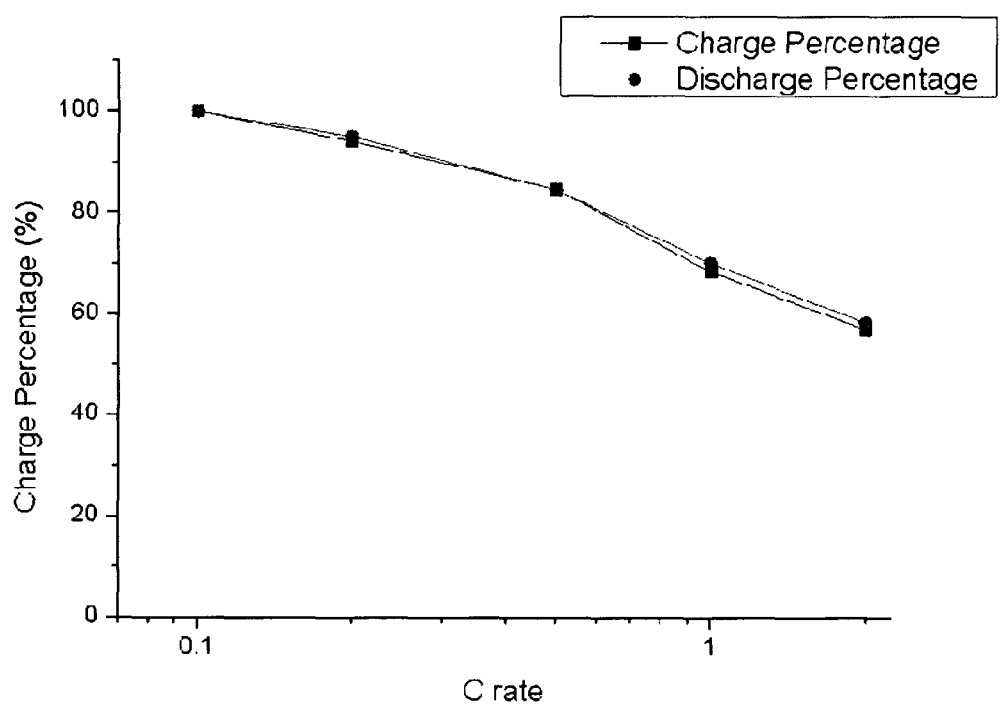
FIG. 9 illustrates power delivery of Poly-NPbIM-1, an exemplary polymer material according to the present invention.

Rate Capability
FIG. 9 shows the power delivery of NPbIm-1 upon discharge at 5 different rates. The material was observed to deliver more than 70% of the original capacity (C/10) upon discharge at a current 10 times higher (C).

High Stability
In FIG. 10 the long term stability of NPbIm-1 is shown. The material completed 1000 cycles and retained more than 85% of the original charge.

No Dissolution in Common Li-Ion Battery Electrolyte Solvents
A sample of the material was put in an ethylene carbonate/dimethyl carbonate mixture for 7 days under magnetic stirring. The powder was then filtered and dried. The weight was unchanged. No discoloration of the solvent was observed.

In view of the above results, it therefore appears that at least problems among problems (1), (3) and (4) mentioned above (electronic conductivity, power density, insolubility in Li-ion electrolytes) are solved by the above-exemplified materials according to the present invention.

The invention claimed is:

1. A compound comprising a structure Red-R-M, wherein:
Red is a redox center;
R is a bridging group; and
M is a monomer giving rise to an electronically conductive polymer,
wherein the redox center contains a group selected from the group consisting of arylenebisimides and indolizines, and wherein the compound has a structure as shown below:

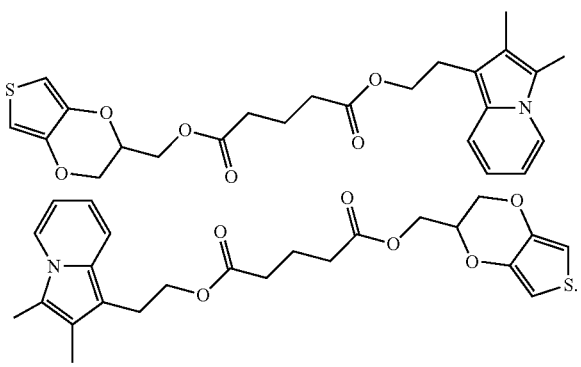

INZ-1

2. A compound comprising a structure Red-R-M, wherein:
Red is a redox center;
R is a bridging group; and
M is a monomer giving rise to an electronically conductive polymer,
wherein the redox center comprises a group selected from the group consisting of indolizines, and
wherein the monomer M comprises a group selected from the group consisting of thiophene, pyrrole, paraphenylenvinylene, furan, carbazole, silole, and fluorene.

3. The compound according to claim 2, wherein the compound has the following structure:

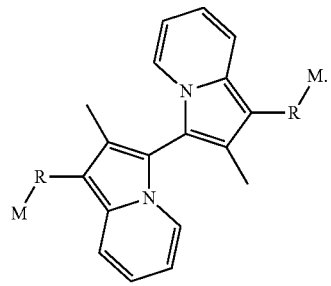

4. The compound according to claim 2, wherein the compound comprises a 3,4-ethylenedioxythiophene (EDOT) group.

5. The compound according to claim 2, wherein the bridge R comprises a linear alkylene chain, a branched alkylene chain, or a glycolic chain, or a combination of functional groups selected from the group consisting of —C(=O)—, —C(=S)—, —O—C(=O)—, —O—C(=S)—, —O—C(=O)—O—, —(C=O)—O—, —C(=S)—O—, —C(=S)—S—, —C(=O)—NR'—, and C(=S)—NR'— where R' is H, alkyl, —SO, —SO₂, or a combination of any linear alkylic chain or branched alkylic chain or glycolic chain separated by one or more of the said functional groups.

6. A polymer obtained by polymerization of a compound according to claim 2.

7. A method for storing electrochemical energy, comprising transferring charge to the polymer according to claim 6 by charge transfer or by adsorption.

8. A lithium-ion battery comprising the polymer according to claim 6.

9. A lithium-ion battery comprising a polymer obtained by polymerization of a compound comprising a structure Red-R-M, wherein:

Red is a redox center;

R is a bridging group; and

M is a monomer giving rise to an electronically conductive polymer, wherein the redox center comprises a group selected from the group consisting of arylenebisimides.

* * * * *